(12) United States Patent
Houser et al.

(10) Patent No.: US 7,132,294 B2
(45) Date of Patent: Nov. 7, 2006

(54) FUNCTIONALIZED SMALL MOLECULES FOR USE IN CHEMICAL SENSORS

(75) Inventors: Eric J. Houser, Nokesville, VA (US); Robert Andrew McGill, Lorton, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 364 days.

(21) Appl. No.: 10/080,403

(22) Filed: Feb. 25, 2002

(65) Prior Publication Data

US 2003/0162987 A1 Aug. 28, 2003

(51) Int. Cl.
*G01N 33/00* (2006.01)
*G01N 33/22* (2006.01)
*G01N 29/24* (2006.01)
*C07F 7/08* (2006.01)
*C07F 7/02* (2006.01)
*C07F 7/12* (2006.01)
*C07C 33/46* (2006.01)
*C07C 33/24* (2006.01)

(52) U.S. Cl. ............... 436/104; 73/31.02; 73/31.05; 422/88; 436/91; 436/103; 436/107; 436/110; 556/431; 556/433; 556/435; 556/443; 556/454; 556/456; 556/465; 556/489; 568/700; 568/715; 568/807; 568/808; 568/811; 568/812

(58) Field of Classification Search ............... 436/91, 436/103–104, 107, 110, 177–178; 422/83, 422/88; 73/31.02, 31.05; 564/433–434; 568/48, 637, 641, 707, 709, 717, 720, 722–723, 568/725–726, 728–729, 700, 715, 807–808, 568/811–812; 556/431, 433, 435, 443, 448, 556/454, 456, 465, 485, 488–489
See application file for complete search history.

(56) References Cited

U.S. PATENT DOCUMENTS

| | | | | |
|---|---|---|---|---|
| 1,971,436 A | * | 8/1934 | Weiler | 549/33 |
| 2,334,408 A | * | 11/1943 | Gump et al. | 568/726 |
| 2,353,725 A | * | 7/1944 | Gump | 568/726 |
| 2,353,735 A | * | 7/1944 | Kunz et al. | 510/388 |
| 2,435,014 A | * | 1/1948 | Niederl | 568/726 |
| 2,455,652 A | * | 12/1948 | Bralley et al. | 526/227 |
| 2,480,556 A | * | 8/1949 | Kleckner et al. | 514/155 |
| 2,565,300 A | * | 8/1951 | Faith et al. | 568/316 |
| 2,606,210 A | * | 8/1952 | Moyle et al. | 568/722 |
| 2,634,297 A | * | 4/1953 | Moyle | 568/718 |
| 2,638,486 A | * | 5/1953 | Chiddix et al. | 568/726 |
| 2,643,265 A | * | 6/1953 | Fon Toy | 558/162 |
| 2,716,129 A | * | 8/1955 | Wilcock et al. | 556/454 |
| 2,730,502 A | * | 1/1956 | Beaver et al. | 510/388 |
| 2,735,872 A | * | 2/1956 | Beaver | 568/720 |
| 3,151,096 A | * | 9/1964 | Kordzinski et al. | 524/511 |
| 3,281,465 A | * | 10/1966 | Stecker | 564/174 |
| 3,340,310 A | * | 9/1967 | Gilbert et al. | 568/726 |
| 3,355,500 A | * | 11/1967 | Farah et al. | 568/637 |
| 3,370,086 A | * | 2/1968 | Gilbert et al. | 560/140 |
| 3,472,879 A | * | 10/1969 | Weiss et al. | 549/462 |
| 3,532,753 A | * | 10/1970 | Gilbert | 564/102 |
| 3,697,569 A | * | 10/1972 | Mironov et al. | 556/449 |
| 3,862,128 A | * | 1/1975 | Greenwald | 548/463 |
| 3,956,402 A | * | 5/1976 | Schellenbaum | 568/729 |
| 4,277,600 A | * | 7/1981 | Mark et al. | 528/204 |
| 4,415,723 A | * | 11/1983 | Hedges et al. | 528/204 |
| 4,415,724 A | * | 11/1983 | Mark et al. | 528/204 |
| 4,778,936 A | * | 10/1988 | Mizuno et al. | 568/720 |
| 4,873,375 A | * | 10/1989 | Kubo et al. | 568/812 |
| 4,883,789 A | * | 11/1989 | Sieburth | 514/63 |
| 4,992,596 A | * | 2/1991 | Jeffries et al. | 568/720 |
| 5,210,247 A | * | 5/1993 | Haberle et al. | 556/413 |
| 5,756,631 A | | 5/1998 | Grate | |
| 6,015,869 A | | 1/2000 | Grate et al. | |

FOREIGN PATENT DOCUMENTS

FR 2784114 * 4/2000

| GB | 669797 | * | 4/1952 |

OTHER PUBLICATIONS

Chang, Y. et al, Polymer Engineering Science 1987, 27, 693-702.*
Snow, A. W. et al, Polymer Preprints 1989, 30, 213-214.*
Abraham, M. H. et al, Journal of the Chemical Society, perkin Transactions 2 1995, 369-378.*
Grate, J. W. et al, SPIE 1995, 2574,71-77.*
McGill, R. A. et al, SPIE 1998, 3392, 384-389.*
Greenblatt, J. et al, Proceedings of the ERDEC Scientific Conference on Chemical and Biological Defense Research, Nov. 18-21, 1997, 843-851; Editor: Berg, Dorothy A.; Publisher: National Technical Information Service, Springfield,Virginia.*
Cunningham, B. T. et al, SPIE 2000, 4036, 151-162.*
Snow, A. W. et al, Journal of Applied Polymer Science 1991, 43, 1659-1671.*
McGill, R. A. et al, CHEMTECH 1994, 27-37.*
McGill, R. A. et al, SPIE 1999, 3392, 384-389.*
Rebiere, D. et al, Sensors and Actuators B 1998, 49, 139-145.*
Houser, E. J. et al, SPIE 1999, 3710, 394-401.*
Demathieu, C. et al, Sensors and Actuators B 200, 62, 1-7.*
Zimmermann, C. et al, Sensors and Actuators B 2001, 76, 86-94.*
Levitsky, I. et al, Analytical Chemistry 2001, 73, 3441-3448.*
Buehler, C. A. et al, Journal of Organic Chemistry 1943, 8, 316-319.*
Buu-Hoï, Ng. Ph. et al, Journal of the Chemical Society 1953, 2612-2614.*
Farah, B. S. et al, Journal of Organic Chemistry 1965, 30, 998-1001.*
Aldrich Chemical Company Catalog 1988, pp. 223-224, 244, 250, 252, 257, 363, 800, 899, 1011, 1382.*
Houser, et al., Rational Materials Design of Sorbent Coatings for Explosives: Applications with Chemical Sensors, Talanta 54 (2001) 469-485.
Fechtenkotter et al, Highly Ordered Columnar Structures from Hexa-peri-hexabenzocorones-Synthesis, X-ray Diffraction, . . . , Angew Chem. Int. Ed. 1999, 38, No. 20, pp. 3039-3042.
Geng et al, Star-like Substituted Hexaarylbenzenes: Synthesis and Mesomorphic Properties, J. Mater. Chem., 2001, 11, pp. 1634-1641.

* cited by examiner

*Primary Examiner*—Arlen Soderquist
(74) *Attorney, Agent, or Firm*—John J. Karasek; Joseph T. Grunkemeyer

(57) ABSTRACT

The invention provides a device for selective molecular recognition, the device comprising a sensing portion, wherein said sensing portion includes a substrate having coated thereon a layer comprising a non-volatile, small molecule compound having at least two pendant and terminal unsaturated groups, each being functionalized with at least one halogen substituted alcohol or phenol functional group. The compound of the invention preferably has one of the following general formulae:

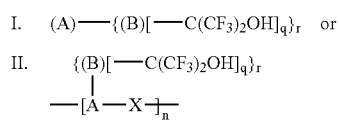

wherein A is a core moiety;

B is a pendant and terminal unsaturated group;

q is at least 1;

r is at least 2;

X is a linking group; and n is an integer designating the number of repeating units from 1 to 3, with the proviso that, if n is greater than 1, then the B groups differ from each other in at least two of the repeating units.

The device is used to detect the molecules of a hydrogen bond accepting vapor such as an organophosphonate or nitroaromatic vapor.

15 Claims, 3 Drawing Sheets

Figure 1. Synthesis of 1,1,1,3,3,3-hexafluoroisopropanol substituted hexaphenylbenzene.

Figure 2. Synthesis of 1,1,1,3,3,3-hexafluoroisopropanol substituted bis(phenpropyl)bis(2-naphthylmethyl)silane.

FUNCTIONALIZED SMALL MOLECULES FOR USE IN CHEMICAL SENSORS

BACKGROUND OF THE INVENTION

1. Field of the Invention

The present invention relates to the detection of noxious chemical species by means of a functionalized small molecule, i.e. non-polymeric sorbent compounds. More particularly, the invention relates to the detection of toxic or explosive chemical vapors, such as chemical agents or nitroaromatic species, by sorbent materials comprising small molecules with halogen substituted alcohol or phenol functional groups.

2. Description of Related Art

Determining and/or monitoring the presence of certain chemical species within an environment, e.g., pollutants, toxic substances and other predetermined compounds, is becoming of increasing importance with respect to such fields as health, environmental protection, resource conservation, and chemical processes. Devices for the molecular recognition of noxious species or other analytes typically include (1) a substrate and (2) a molecular recognition coating upon the substrate. These devices may be used, for example, in chemical vapor sensing or the selective separation of gases by gas chromatography. Small molecular recognition devices are described in Grate et al., *Sensors and Actuators B*, 3, 85–111 (1991) and Grate et al., *Analytical Chemistry*, Vol. 65, No. 14, Jul. 15, 1993, both of which are incorporated herein by reference.

Frequently, the substrate is a piezoelectric material or a waveguide, which can detect small changes in mass. One illustrative example of a device relying upon molecular recognition as a surface is known as a surface acoustic wave (SAW) sensor. SAW devices function by generating mechanical surface waves on a thin slab of a piezoelectric material, such as quartz, that oscillates at a characteristic resonant frequency when placed in a feedback circuit with a radio frequency amplifier. The oscillator frequency is measurably altered by small changes in mass and/or elastic modulus at the surface of the SAW device.

SAW devices can be adapted to a variety of gas-phase analytical problems by designing or selecting specific coatings for particular applications. The use of chemoselective polymers for chemical sensor application is well established as a way to increase the sensitivity and selectivity of a chemical sensor with respect to specific classes or types of analytes. Typically, a chemoselective polymer is designed to contain functional groups that can interact preferentially with the target analyte through dipole-dipole, Van der Waal's, or hydrogen bonding forces. For example, strong hydrogen bond donating characteristics are important for the detection of species that are hydrogen bond acceptors, such as toxic organophosphorus compounds. Increasing the density of available hydrogen bond acidic binding sites in the coating of a sensor results in an increase in sensitivity.

Chemoselective films or coatings used with chemical sensors have been described by McGill et al. in *Chemtech*, Vol. 24, No. 9, 27–37 (1994). The materials used as the chemically active, selectively absorbent layer of a molecular recognition device have often been polymers, as described in Hansani in *Polymer Films in Sensor Applications* (Technomic, Lancaster, Pa. 1995). For example, Ting et al. investigated polystyrene substituted with hexafluoroisopropanol (HFIP) groups for its compatibility with other polymers in *Journal of Polymer Science: Polymer Letters Edition*, Vol. 18, 201–209 (1980). Later, Chang et al. and Barlow et al. investigated a similar material for its use as a sorbent for organophosphorus vapors, and examined its behavior on a bulk quartz crystal monitor device in *Polymer Engineering and Science*, Vol. 27, No. 10, 693–702 and 703–15 (1987). Snow et al. (*NRL Letter Report*, 6210–884A) and Sprague et al. (*Proceedings of the 1987 U.S. Army Chemical Research Development and Engineering Center Scientific Conference on Chemical Defense Research*, page 1241) reported making materials containing HFIP that were based on polystyrene and poly(isoprene) polymer backbones, where the HFIP provided strong hydrogen bond acidic properties. These materials were used as coatings on molecular recognition devices, such as SAW sensors, and showed high sensitivity for organophosphorus vapors. However, both the parent polymers and the HFIP-containing materials were glassy or crystalline at room temperature. Because vapor diffusion is slowed in glassy or crystalline materials, the sensors produced were slow to respond and recover. Additional information is reported in *Polym. Eng. Sci.*, 27, 693 and 703–715 (1987).

Grate et al. in *Analytical Chemistry*, Vol. 60, No. 9, 869–75 (1988), discloses a polymeric compound called "fluoropolyol" (FPOL), which is useful for detecting organophosphorus compounds. FPOL has the formula:

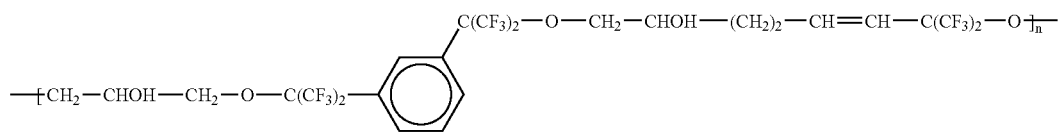

An HFIP-containing polymer based on a polysiloxane backbone was described and demonstrated to be a good hydrogen-bond acid by Abraham et al., "Hydrogen Bonding XXIX. The Characterisation of Fourteen Sorbent Coatings for Chemical Microsensors Using a New Solvation Equation", *J. Chem. Soc., Perkin Trans.* 2, 369–78 (1995). The polysiloxane backbone provided a material with a Tg well below room temperature, however, other physical properties were not shown.

Grate, U.S. Pat. No. 5,756,631, discloses the use of hexafluoroalcohol-substituted siloxane polymers having the structure:

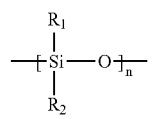

wherein $R_2$ has the formula $-(CH_2)_{m-1}-CH=CH-CH_2-C(CF_3)_2-OH$, and n is an integer greater than 1.

Grate et al., U.S. Pat. No. 6,015,869 discloses a strongly hydrogen bonding acidic, sorbent oligomer or polymer having a glass-to-rubber transition temperature below 25° C. The polymer has (1) fluoroalkyl-substituted bisphenol segments containing interactive groups and (2) oligodimethyl-siloxane segments. These siloxane polymers are said to provide improved coatings and vapor sorption compositions for chemical sensors that are sensitive, reversible and capable of selective absorptions for particular vapors, particularly the hydrogen bond accepting vapors, such as organophosphorus compounds. However, these are still polymeric materials and, like all polymers, they can vary significantly from batch to batch in precise composition, purity and yield.

The inventors have now discovered a class of small molecules, rather than siloxane polymers, that can, in fact, be combined with polymeric matrices to produce composite hydrogen bond acidic coatings for chemical sensor applications. Using small molecules that are highly functionalized can result in significant sensitivity improvements. The host polymer matrix may or may not be functionalized with hydrogen bond acid groups. Thus, the functionalized small molecules described herein can improve the sensitivity of a sensor coating by increasing the density of hydrogen bond acid groups within the coating material.

Further, the chemoselective small molecules of the invention exhibit improved sensitivity to vapors of organophosphorus and nitroaromatic species, and are thus also useful for detecting the presence of these toxic materials. Conventional explosives, such as trinitrotoluene (TNT), hexahydro-1,3,5-trinitro-1,3,5-triazine (RDX), and octahydro-1,3,5,7-tetranitro-1,3,5,7-tetrazocine (HMX), may be contained in unexploded munitions, e.g., buried below the surface of the ground. Such munitions exude or leak vapors of the explosive. These vapors are typically concentrated in the surrounding soil and then migrate to the surface where they can be detected by the compounds, devices and methods of the invention. A similar situation exists for unexploded ordnance (UXO) found underwater.

SUMMARY OF THE INVENTION

According to a first aspect of the present invention, there is provided a non-volatile small molecular compound having at least two pendant and terminal unsaturated groups, each being functionalized with at least one halogen substituted alcohol or phenol functional group.

According to a second aspect of the invention, there is provided a device for selective molecular recognition, the device comprising a sensing portion, wherein the sensing portion includes a substrate having coated thereon a layer, the layer containing the small molecular compound of the invention.

According to another aspect of the invention, there is provided a method of detecting a hydrogen bond accepting vapor or a nitroaromatic vapor, comprising the steps of:
(a) contacting the molecules of such a vapor with the sensing portion of the device of the invention;
(b) collecting the molecules on the layer of the device, the molecules altering a specific physical property of the layer; and
(c) detecting the amount of change with respect to the physical property from before the contacting step (a) and after the collecting step (b).

According to a yet another aspect of the invention, there is provided a solution for preparing a chemical vapor sensor comprising (a) an amount of the small molecule compound of the invention effective to enhance the sensitivity of the sensor to hydrogen bond accepting vapors or nitroaromatic compounds and (b) a solvent for the compound.

DETAILED DESCRIPTION OF THE INVENTION

Figure 1:
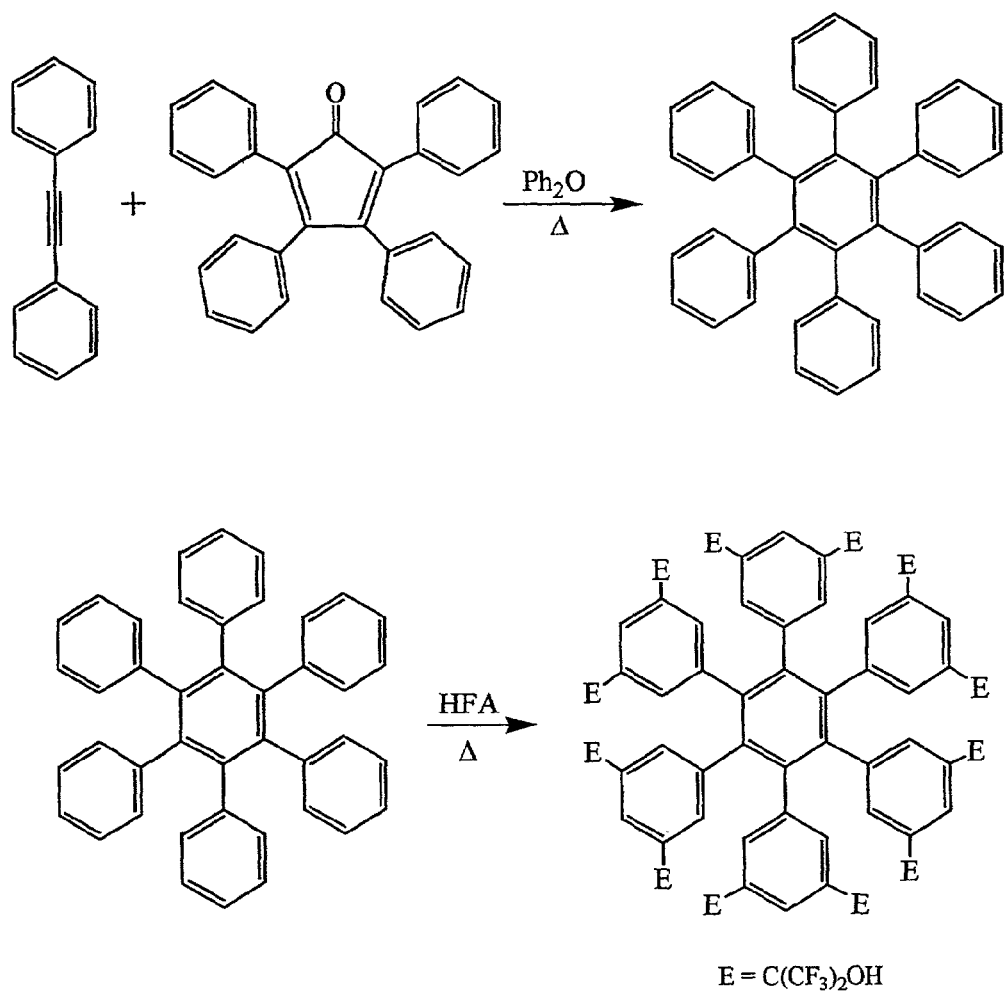
FIG. 1 shows the synthesis of a compound of the invention, specifically, synthesis of 1,1,1,3,3,3-hexafluoroisopropanol substituted hexaphenylbenzene.

The compound of the invention is a non-volatile, small molecular compound having at least one pendant and terminal unsaturated group, each being functionalized with at least one halogen substituted alcohol or phenol functional group. By "non-volatile" is meant that the compound exhibits a volatility no greater than 0.1% when under dynamic conditions of flowing clean air over a SAW device in use at a temperature of about 70° C. for 24 hours. By "small molecule" is meant that the compound has no more than three identical repeating units.

The compound may be entirely organic or organometallic in composition. A preferred class of such compounds can be represented by one of the two following general formulae:

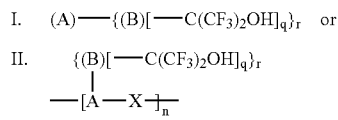

wherein A is an atom, organic, organometallic or inorganic core or backbone entity;
B is a pendant and terminal unsaturated group;
q is at least 1, preferably from 1 to 3;
r is at least 2, preferably from 3 to 12;
X is a linking group; and
n is an integer designating the number of repeating units from 1 to 3, with the proviso that, if n is greater than 1, then the B groups differ from each other in at least two of the repeating units.

A, the core entity, may be an atom or an organic, inorganic, or organometallic moiety containing such atoms as silicon, disiloxane, benzene, ferrocene or the like. Examples of useful "A" groups include alkylenes, such as ethylene, n-propylene, isopropylene, tert-butylene, n-hexylene, n-dodecylene, hexadiene and the like; alkylene silicon moieties such as -Si-alkylene-Si-, -alkylene-Si-alkylene-, alkylene-Si-alkylene-Si-alkylene and the like; alkenylene, such as n-butenylene, cinnamylene, hexadienylene and the like; cycloalkylene, such as cyclobutylene, cyclopentylene, cyclohexylene, cyclooctylene and the like; cycloalkenylene, such as cyclohexadienylene, cyclooctatetraenylene and the like; arylene, such as phenylene, biphenylene, durylene, naphthalene, anthracenylene, terphenylene and the like; -Si-arylene-Si-, arylene-Si-arylene-, -arylene-Si-arylene-Si-arylene- and the like; and heterocyclene, such as thienylene, furylene, pyrrolylene and the like; organometallic, such as ferrocenylene, ruthenocenylene, titanocenylene and the like. Preferably, however, A is alkylene, arylene, or -Si-alkylene-Si. Most preferably, A is either phenylene or -Si-(CH$_2$)$_n$-Si- wherein n is 1 to 4.

B in the above formula is a pendant and terminal unsaturated group. By "unsaturated" is meant any site of unsaturation, such as, for example, a double or triple bond and an aromatic ring. Examples of B include ethynyl, allyl or propenyl, 2-methylpropenyl, amylenyl and the like; cycloalkylenyl such as cyclpentadienyl, cyclohexadienyl and the like; arylene, such as phenylene, biphenylene, anthracenyl, furylene and the like; alkylarylene, such as benzylene, phenethyl, 1-phenylpropylene, xylylene, terephthalene and the like; and alkynylene, such as propynyl, butadiynyl and the like, Preferably, B is an arylene or alkylarylene group. Even more preferably, B is either phenylene or

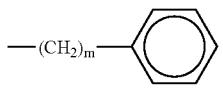

wherein m is 1 to 4, preferably 1 to 3.

X (in Formula II) can any of a wide variety of linking groups, such as a direct bond; an arylene such as phenylene, naphthalene, biphenylene, anthracenyl, furylene and the like; hydrocarbylene, for example, alkylenes, such as ethylene, n-propylene, isopropylene, tert-butylene, n-hexylene, n-dodecylene, hexadiene and the like; alkylarylene, such as benzylene, phenethyl, 1-phenylpropylene, xylylene, terephthalene and the like; alkynylene, such as propynyl, butadiynyl and the like; or a heteroatom such as silicon, oxygen, nitrogen or phosphorus; or combinations thereof.

Further, in Formula II, when the recurring units

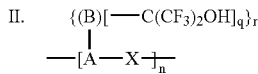

are taken together, they may form a homocyclic or heterocyclic ring of —[A—X]— linkages. Examples of such rings include cycloalkyl, cycloalkenyl, or aromatic rings. Preferably, when the —[A—X]— linkages, taken together, form a ring, the ring is aromatic, such as a phenyl ring.

The novel compounds of the invention are strongly hydrogen bond donating. They are useful in a variety of applications, and especially as a coating material on chemical sensors. They are very sensitive for hydrogen bond accepting vapors, such as organophosphorus and nitro-substituted compounds.

Figure 2:
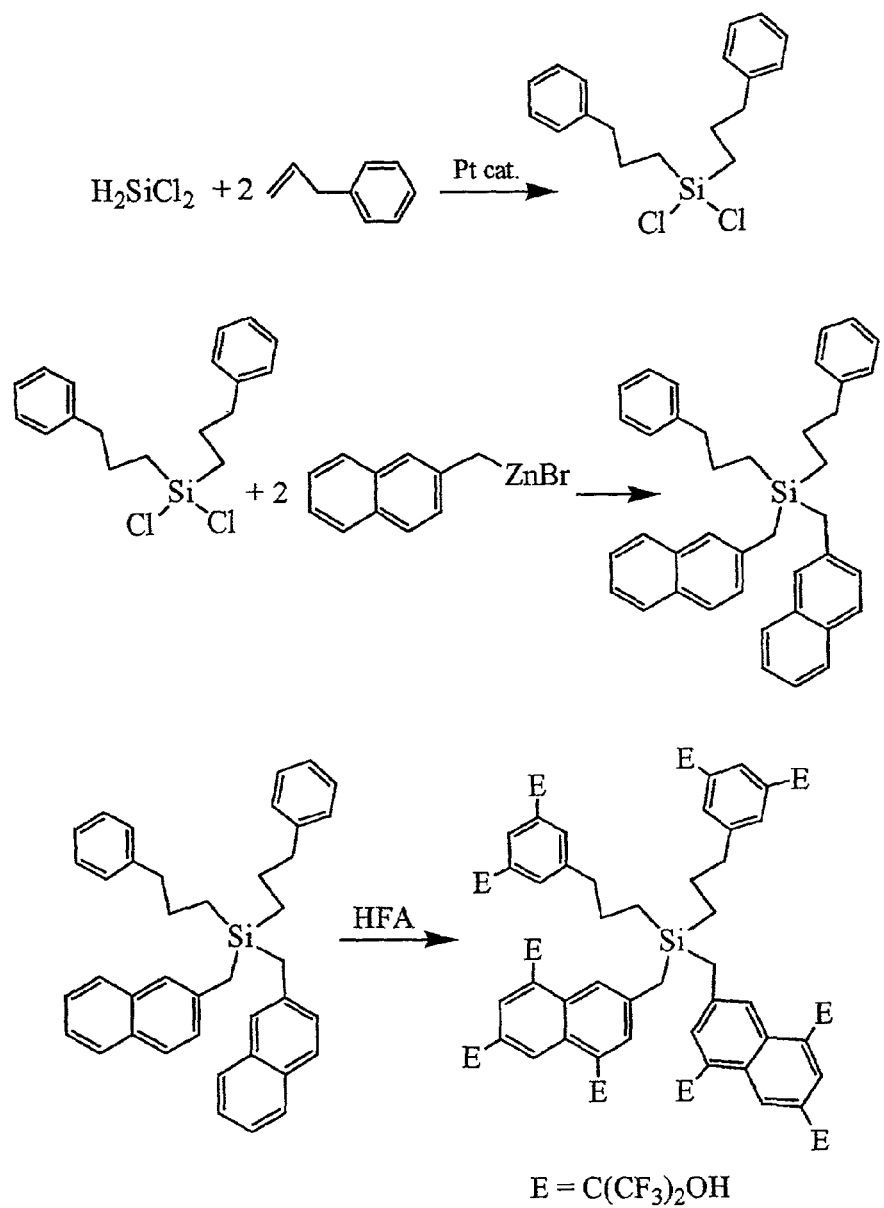
FIG. 2 shows the synthesis of another compound of the invention, specifically, synthesis of 1,1,1,3,3,3-hexafluoroisopropanol substituted bis(phenpropyl)bis(2-naphthylmethyl)silane.
Figure 3:
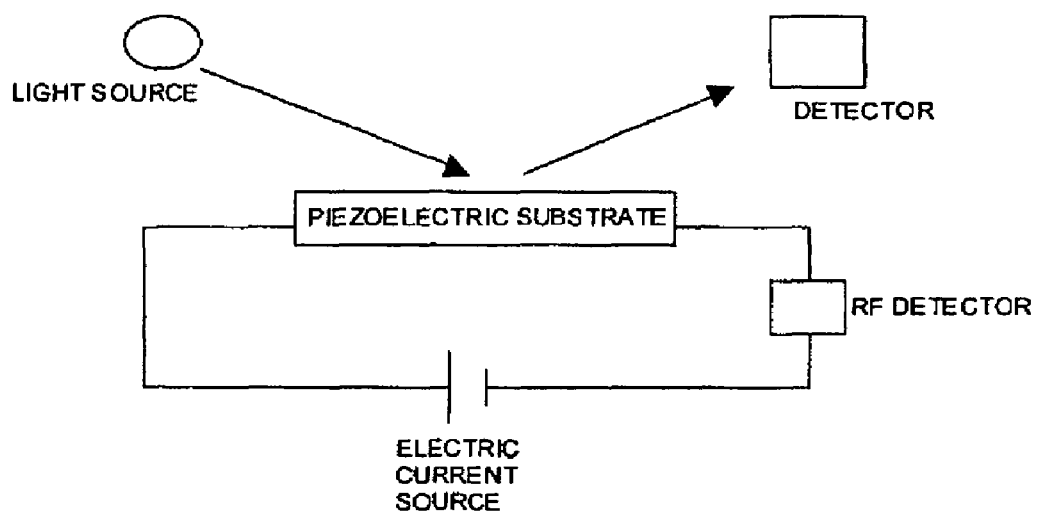
FIG. 3 schematically illustrates a molecular recognition device.

The compounds of the invention can be synthesized by attaching a halogen substituted alcohol or phenol functional group, such as hexafluoroisopropanol, to the parent molecule, possibly comprising a core A and always containing a number of pendant and terminal unsaturated groups. An example of the reactivity of perfluoroketones with terminally unsaturated groups is described by Urry et al., *J. Org. Chem.*, Vol. 33, 2302–2310 (1968), incorporated herein by reference. The synthesis of two such compounds of the invention is shown in FIGS. 1 and 2. These compounds are typically synthesized in high yield.

Once synthesized, these small molecules, which may or may not be mixed with a polymer matrix, can be coated to a controlled film thickness on a substrate, either alone or mixed with a solvent or similarly functionalized polymer to form a mixture having the desired Tg. Examples of such polymers include both linear and polybranched, cascade or dendrimeric polymers, such as polysiloxane, polycarbosilanes, polyisobutylene, polybutadiene, or mixtures thereof. The Tg of the resulting mixture should exhibit a Tg below the operating temperature of the sensor, for example, within the range of about 0–100° C., preferably between about 20–50° C. Useful substrates include those that allow an electronic means to monitor the physical or chemical properties of thin, chemically sorbent films as they are exposed to an analyte, either from a condensed or gaseous phase.

Examples of suitable chemical transducers include acoustic wave devices, such as surface acoustic wave (SAW), thickness shear mode (TSM), or bulk acoustic wave (BAW) substrates; optical waveguides (OW) used in transmission, reflectance or excitation modes, such as fiber optic (FO), total internal reflectance fluorimeter (TIRF), or surface plasmon resonance (SPR) devices; and devices that modulate or monitor the electrical properties of thin sorbent films, such as amperometric, conductometric or potentiometric-based devices. Some devices, such as micromachined cantilever devices, can be operated in resonant or bending mode. In the bending mode application of cantilevers, the sorbent film, when exposed to an analyte, causes bending of the substrate to which the sorbent film is coated. This can then be monitored by a variety of means, such as the piezoresistive or capacitive properties of the centilever or the optical deflection of light from a reflective portion of the cantilever surfaces of silica capillaries.

The principle of operation of an acoustic wave device transducer involves the production of an acoustic wave that is generated on the surface or through the bulk of a substrate material and allowed to propagate. To generate the acoustic wave typically requires a piezoelectric material. Applying a time varying electric field to the piezoelectric material will cause a synchronous mechanical deformation of the substrate with a coincident generation of an acoustic wave in the material. The time varying electric field is generated in the surface by the action of the time varying electrical field applied through one or more electrodes that are connected to the piezoelectric material via one or more metal wire bonds and to an electrical circuit. Another electrode or electrodes receives the wave at a distance from the first electrode or electrodes. The second electrode or electrodes is also connected via metal wire bonds to the electrical circuit and the piezoelectric material. Such devices are operable in a frequency range of about 2 kilohertz to 10 gigahertz, preferably from about 0.2 megahertz to about 2 gigahertz and, more preferably, in the range of between about 1 to 900 megahertz.

For piezoelectric sensors, piezoelectric substrates known in the art are useful in accordance with the invention, e.g., ST-cut quartz. In addition to quartz crystals, piezoelectric ceramics, such as those of the barium titanate and lead titanate zirconate families, are suitable substrates. These include LiNbO$_3$; BaTiO$_3$; 95 wt.% BaTiO$_3$/5% GaTiO$_3$; 80 wt.% BaTiO$_3$/12% PbTiO$_3$/8% CaTiO$_3$; PbNb$_2$O$_6$; Na$_{0.5}$K$_{0.5}$NbO$_3$; Pb$_{0.94}$Sr$_{0.06}$(Ti$_{0.48}$Sr$_{0.52}$)O$_3$; and Pb$_{0.94}$(Ti$_{0.48}$Sr$_{0.52}$)O$_3$. In some cases, the substrate may comprise a piezoelectric coating material, such as ZnO or AlN, applied to a non-piezoelectric material, such as silicon. The piezoelectric properties of these and other suitable materials are provided in *CRC Handbook of Materials Science,* Vol. III. Charles T. Lynch, CRC Press; Boca Raton, 198 (1975).

The sensing portion of an acoustic wave device of the invention is the area under the chemoselective layer, where the chemoselective layer covers the transducer. The area of the sensing portion of such a device can be as large as about 4 cm$^2$.

An optical waveguide chemical sensor consists of a light source, an optical waveguide, a chemoselective film or layer, and a detector to analyze the light after interacting with the layer. The waveguide is used to propagate light to a sensing portion of the device that contains the chemoselective layer. The light travels toward this coating and interacts with it. If the analyte being detected is present in the layer, the optical characteristics of the light may be altered, and the change is detected by an optical detector.

An optical chemical sensor, commonly referred to as an optrode, includes a light source such as a semiconductor laser, light-emitting diode, or a halogen lamp; an optical waveguide such as a fiber optic or a planar waveguide substrate; a chemoselective layer deposited on the sensing portion of the optrode exposed to an analyte; and a detector to monitor the optical characteristics of the optrode. Sorption of the analyte to the chemoselective layer modifies the optical characteristics of the optrode, and this is detected as a change in refractive index or light intensity at one or more wavelengths of light. Thus, for optical sensors, optical fibers and optical wave guides are useful and are known in the art.

Fiber optic waveguides for sensor applications are commonly manufactured from silica glass or quartz as the core of the fiber. Surrounding this core is a cladding material that exhibits a lower refractive index than the cladding to achieve internal reflectance. The chemoselective layer is typically applied at the distal tip of the fiber optic or along the side of the fiber optic where a portion of the cladding material has been removed.

Planar waveguide optical sensors use a planar substrate device as a light guide. The use of a planar waveguide normally involves the use of evanescent wave techniques to take advantage of the large active surface area. Many of these sensors use the fluorescent properties of a chemoselective layer and are thus called Total Internal Reflection Fluorescence (TIRF) sensors.

Preferably, SAW devices are used as the substrate for the device of the invention. Particularly preferred SAW devices are 915 MHz two-port resonators made of ST-cut quartz with aluminum metallization and a thin silicon dioxide overcoat. SAW resonators and oscillator electronics to drive them are available from RFM, Dallas, Tex.

Before application of a coating to form the sensor portion of the device of the invention, the substrate is cleaned. The cleaning procedure typically involves rinsing the device in an organic solvent and then subjecting it to plasma cleaning, as is well known. Optionally, the substrate can be silanized with a material such as diphenyltetramethyldisilazane (DPTMS) by immersing the cleaned substrate surface in liquid DPTMS, placing the immersed surface into a partially evacuated chamber while heating the device to about 170° C. for about 12 hours. The silanized substrate is then removed and solvent cleaned with, for example, toluene, methanol, chloroform, or a physical or serial combination thereof, before applying the chemoselective layer to the sensor portion of the device.

The method used for coating the compounds of the invention onto a substrate is not critical, and various coating methods known in the art may be used. Typically, the coating is applied to the substrate in solution, either by dipping, spraying or painting, or a laser deposition process such as MAPLE, preferably by an airbrush or spin coating process. For micron scale devices, the use of the MAPLE coating process is preferred. The concentration of the compound of the invention in the coating solution should be sufficient to provide the viscosity most appropriate for the selected method of coating, and may easily be determined empirically. The solvent used, although not critical, should be sufficiently volatile as to facilitate quick and easy removal, but not so volatile as the complicate the handling of the coating solution prior to being deposited on the substrate. Examples of useful solvents include, for example, hexane, chloroform, toluene, xylene, dichloromethane, and tetrahydrofuran. J. W. Grate and R. A. McGill in *Analytical Chemistry,* Vol. 67. No. 21, 4015–19 (1995), the subject of which is incorporated herein by reference, describe making chemical acoustic wave detectors by applying a thin film to a surface acoustic wave (SAW) device.

The thickness of the chemoselective layer preferably does not exceed that which would reduce the frequency of a chemical sensor operating at 250 megahertz by about 250 kilohertz and, typically, is in the range of about 0.5 nm to 10 microns, preferably in the range of 1 to 300 nm, including both the compound mixed with any additional polymeric material being used.

The coating may comprise a single layer or multiple layers. With multiple layers, a layer containing the compound of the invention may be combined with at least one other layer that provides pores suitable for physically eliminating some chemical species of large size that are not to be monitored.

The process of sorption plays a key role in the performance of chemical sensors for gas phase analysis. For example, microsensors, which consist of a physical transducer and a selective sorbent layer, sense changes in the physical properties, such as mass, in the sorbent layer on the surface of the transducer, due to the sorption of analyte molecules from the gas phase into the sorbent layer. Coating properties that are known to elicit a detectable SAW sensor response are mass (i.e., as determined by the thickness and density of the coating), elasticity, viscoelasticity, conductivity, and dielectric constant. Changes in these properties can also result in changes in the attenuation (i.e., loss of acoustic power) of the wave. In some situations, monitoring attenuation may be preferable to monitoring velocity. Alternatively, there are some situations where simultaneously monitoring both velocity and attenuation can be useful. In any event, it is the modification of the sensed properties of the sorbent layer, as a result of sorption, that results in the detection of analyte molecules in the gas phase. SAW devices coated with compounds of the invention are capable of detecting mass changes as low as about 100 pg/cm$^2$. Further, vapor diffusion is rapid.

Sensor selectivity, the ability to detect a chemical species in an environment containing other chemical species, is generally determined by the ability of the coated layer to specifically sorb the species to be detected to the exclusion of almost all others. For most coatings, selectivity is obtained based on providing stronger chemical interactions between the coated layer and the target species than occurs between the layer and species that are not to be detected. The method of selectively detecting the presence of a chemical entity within an environment comprises (a) placing the sensing portion of the device of the invention in the environment and (b) detecting changes in the coated layer of the sensing portion of the device. The environment is generally a fluid, i.e. gaseous or liquid.

More than one device may be provided. For example, a plurality of sensor portions could be used in a sensor array with, e.g., associated control devices and software, in a manner similar to conventional procedures employed with sensor arrays.

After an initial sensing has taken place, the coated sensor layer can be purged or cleaned by a second stream, allowing sensing of a new third stream to take place. For example, clean air, nitrogen, water- or acid-base solutions could be used as purging or cleaning solutions, depending on the environment, the species being detected, and the nature of the layer.

In the devices and methods of the invention, the compounds are good sorbents for hydrogen bond basic vapors, such as organophosphorus and nitro-substituted compounds. It is expected that the devices of the invention could weigh less than 1 pound and could, therefore, be easily mounted on a remote or robotic vehicle for detection of buried explosives, munitions, or chemical weapons. Alternatively, such a device would also be useful for remotely detecting explosives or chemical weapons secreted upon a person intending the destruction of private property and/or personnel, such as, for example, at crowded public places like airports or arenas where terrorist activity may be suspected.

It desired, it is possible to increase the concentration of explosive vapors contained in the area being monitored, i.e., speed up their release from buried or otherwise hidden munitions or explosives, by irradiating the area with electromagnetic radiation. For example, a beam-forming antenna could be employed to direct high frequency to long wavelength microwave radiation at the area suspected of containing buried munitions, such as landmines. This will gently warm the area being checked and increase explosive vapor leakage prior to testing with the device of the invention. Increasing the concentration of vapor in the soil or other environment surrounding a munition will produce a stronger signal following the reaction with sensor portion of the device of the invention.

The chemoselective, small molecule compounds of the invention exhibit high selectivity and sensitivity toward vapors of organophosphonate and nitro-substituted compounds, due at least in part to the sensitivity and selectivity of the halogen substituted alcohol or phenol functional groups that are present. The presence of these functional groups is also directly responsibility for the sensitivity of these materials to hydrogen bond basic vapors. The functionalized small molecules of the invention also have the advantage of high-yield preparation methods, ready purification, in addition to having an increased density of functional groups, as compared with polymeric coatings, Moreover, the flexibility in the synthesis of these materials allows one to tailor a wide variety of related chemoselective compounds.

EXAMPLES

Example 1

Preparation of hexa(bis-3,5-hexafluoroisopropanol-phenyl)benzene

A stainless steel cylinder containing a mixture hexaphenylbenzene (2.5 g) and a catalytic amount of $AlCl_3$ (0.10 g) in a saturated hydrocarbon solvent (100 mL) is charged with hexafluoroacetone (~10 g). The resulting mixture is heated to 60° C. for 48 hours. The volatiles are then removed in vacuo and the resulting pale brown solid is washed with saturated aqueous ammonium chloride and recrystallized from $CH_2Cl_2$ and hexanes.

Example 2

Preparation of 1,3,5-tri(tris-3,5-hexafluoroisopropanol-2-naphthylmethyl)benzene.

A stainless steel cylinder containing a mixture 1,3,5-tris (2-naphthylmethyl)benzene (3.0 g) and a catalytic amount of $AlCl_3$ (0.10 g) in a saturated hydrocarbon solvent (100 mL) is charged with hexafluoroacetone (~10 g). The resulting mixture is heated to 60° C. for 48 hours. The volatiles are then removed in vacuo and the resulting pale brown solid is washed with saturated aqueous ammonium chloride and recrystallized from $CH_2Cl_2$ and hexanes.

Example 3

Applying a Thin Film to a SAW Device

SAW devices are cleaned in a Harrick plasma cleaner prior to polymer film application. Spray-coated films of the compound of FIG. 1 in chloroform are applied to a SAW device using an airbrush supplied with compressed dry nitrogen. The frequency change of the SAW device operating in an oscillator circuit is monitored during deposition, using the change in frequency as a measure of the amount of material applied. After applications, the films are annealed at 50° C. overnight in an oven. Spray-coated films are examined by optical microscopy with a Nikon microscope using reflected light Nomarski differential contrast.

Example 4

Detection of Basic Vapors with a Compound-Coated SAW Device

The compounds of FIGS. 1 and 2 are applied to SAW devices and tested against organic vapors at various concentrations. Upon exposure to a vapor, the coated acoustic wave devices undergo a shift in frequency that is proportional to the amount of vapor sorbed by the compound. Times to steady state response, corresponding to equilibrium partitioning of the vapor into the compound layer, are typically under 30 seconds using a vapor delivery system. From frequency shift data for a vapor at multiple concentrations, calibration curves are constructed. The calibration curves are nonlinear, which is consistent with hydrogen-bonding interactions at a finite number of sites in the compound.

Example 5

Coating a Capillary Column

A solution of the compound of FIG. 2 in chloroform is used to coat the interior surface of several one-meter silica capillary columns with an inside diameter of 100 microns. The procedure to coat a 100-micron ID column from Fused Silica Intermediate Polarity (part number 2-5745, Supelco, Pa.) involves filling the capillary with a solution of the compound, closing one end of the capillary, and pulling a vacuum off the other end of the capillary at a fixed temperature. The solution-filled column is placed into a gas chromatographic oven stabilized at 30° C. to control the temperature. A vacuum is then pulled using an oil-free Teflon-coated diaphragm pump (Fisher part number 13-875-217C). vacuum of −70 kPa), typically being applied for about 15–20 hours.

The thickness and thickness uniformity are verified by cutting a coated column into several pieces and looking at the cross sections using a high power optical microscope. The thickness of one micron is usually in good agreement with the theoretical film thickness.

Example 6

Optical Fiber Drawing and Cladding

The compound of FIG. 2 is combined with a solvent to form a viscous mixture, which a stirred until well blended and degassed under vacuum. The viscous mixture is applied to a fused silica fiber as it is freshly drawn from a Heathway fiber drawing apparatus through a 2–5 mm Sandcliff cladding cup, and into a 45 cm long clamshell furnace for curing. The viscous mixture is supplied to the cladding cup under a pressure of about 0.8 to about 1.5 psi. The optimal furnace temperature and fiber draw speed are typically about 520° C. and 8–9 m/min respectively. These relatively slow draw rates are usually used for manual control of the drawing conditions, but sometimes result in variable core diameters and coating thickness. However, when used with the other conditions described, a fairly uniform coating that is light yellow in color and slightly tacky to the touch is usually obtained. As the viscosity of the solution of the compound increases during the fiber drawing, the delivery pressure should be increased over the course of filling, usually about two hours.

Half-meter to one meter sections are hand selected for quality. The best fiber sections made under these conditions have a smooth coating over a 180-micron diameter core about 25 microns thick. All are usually effective in guiding light.

Example 7

Preparation of mixture of poly[bis(hexafluoroisopropanol-allyl)siloxane] and hexa(bis-3,5-hexafluoroisopropanol-phenyl)benzene.

To a 250 mL flask, samples of poly[bis(hexafluoroisopropanol-allyl)siloxane] (1.0 g) and hexa(bis-3,5-hexafluoroisopropanol-phenyl)benzene (0.25 g) were combined and dissolved in $CHCl_3$ (30 mL). After stirring for 10 minutes, the solvent was removed and the resulting mixture was ready for use as a sensor coating.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the generally inventive concept as defined by the appended claims and their equivalents.

What is claimed is:

1. A molecular recognition device comprising a substrate, a molecular recognition layer disposed on said substrate, and a detector for analyzing changes in said layer, said layer comprising an effective amount of a compound to improve the sensitivity of the molecular recognition layer, the compound having following general formula:

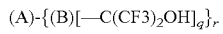

wherein: A is a core moiety having no more than three identical repeating units that are bonded to a (B)[—C(CF3)$_2$OH]$_q$ group and selected from alkylene, an alkylene-silicon moiety, alkenylene, cycloalkylene, cycloalkenylene, arylene, an arylene-silicon moiety, heterocyclene, an organometallic moiety, and linear or cyclic alternating combinations thereof with up to three oxygen, nitrogen, or phosphorus atoms;

B is a pendant and terminal unsaturated group;

q is at least 1; and r is at least 2.

2. The device of claim 1 wherein A is selected from the group consisting of alkylene, arylene, and -Si-alkylene-Si groups.

3. The device of claim 1 wherein A is selected from the group consisting of phenylene and -Si-$(CH_2)_p$-Si- groups wherein p is 2 to 4.

4. The device of claim 3 wherein B is selected from the group consisting of arylene and alkylarylene groups.

5. The device of claim 3 wherein B is phenylene.

6. The device of claim 1 wherein said substrate is piezoelectric; and said device further includes a light source for imparting light to said substrate, an electric current source for imparting current to said substrate, and a detector to analyze the light after interacting with the layer.

7. The device of claim 1 wherein thickness of said layer is 1 to 300 mm.

8. The device of claim 1 wherein said compound has volatility no greater than 0.1% when under dynamic conditions of flowing clean air over said device in use at a temperature of about 70° C. for 24 hours.

9. A solution for preparing a chemical vapor sensor comprising:

(a) a compound selected from hexakis[2,4-di(1,1,1,3,3,3-hexafluoroisopropan-2-ol)phenyl]benzene, bis[2,4-di(1,1,1,3,3,3-hexafluoroisopropan-2-ol)phenylpropyl]bis(4,6,8-tri(1,1,1,3,3,3-hexafluoroisopropan-2-ol)-2-naphthylmethyl)silane, and combinations thereof;

(b) non-aqueous solvent for said compound.

10. A method of detecting the molecules of a hydrogen bond accepting vapor or a nitroaromatic vapor, comprising the steps of:

(a) contacting the molecules of said vapor with a device comprising a sensing portion, wherein said sensing portion includes a substrate having coated thereon a layer, said layer comprising an effective amount of a compound to improve the sensitivity of the sensing portion, the compound having the general formula:

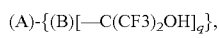

wherein: A is a core moiety having no more than three identical repeating units that are bonded to a (B)[—C(CF3)$_2$OH]$_q$ group and selected from alkylene, an alkylene-silicon moiety, alkenylene, cycloalkylene, cycloalkenylene, arylene, an arylene-silicon moiety, heterocyclene, an organometallic moiety, and linear or cyclic alternating combinations thereof with up to three oxygen, nitrogen, or phosphorus atoms;

B is a pendant and terminal unsaturated group;

q is at least 1; and r is at least 2;

(b) collecting said molecules on said layer wherein said molecules alter a specific physical property of said layer; and (c) detecting the amount of change in the physical property from before said contacting step (b) and after said collecting step (b).

11. The method of claim 10 wherein A selected from the group consisting of alkylene, arylene, and -Si-alkylene-Si groups.

12. The method of claim 10 wherein A is selected from, the group consisting of phenylene and -Si—$(CH_2)_p$-Si- groups, wherein p is 2 to 4.

13. The method of claim 10 wherein B is selected from the group of arylene and alkylarylene groups.

14. The method of claim 10 wherein B is phenylene.

15. The method of claim 10 wherein said compound has volatility no greater than 0.1% when under dynamic conditions of flowing clean air over device in use at a temperature of 70° C. for 24 hours.

* * * * *